(12) United States Patent
Gerrits

(10) Patent No.: US 10,835,358 B2
(45) Date of Patent: Nov. 17, 2020

(54) DENTAL APPLIANCE CLEANING SYSTEM WITH REDUCED CROSS CONTAMINATION

(71) Applicant: Michele Gerrits, Kaukauna, WI (US)

(72) Inventor: Michele Gerrits, Kaukauna, WI (US)

( * ) Notice: Subject to any disclaimer, the term of this patent is extended or adjusted under 35 U.S.C. 154(b) by 0 days.

(21) Appl. No.: 16/242,188

(22) Filed: Jan. 8, 2019

(65) Prior Publication Data
US 2019/0209278 A1 Jul. 11, 2019

Related U.S. Application Data

(60) Provisional application No. 62/615,759, filed on Jan. 10, 2018.

(51) Int. Cl.
| | | |
|---|---|---|
| *A61C 19/00* | (2006.01) | |
| *B08B 3/12* | (2006.01) | |
| *A61Q 11/02* | (2006.01) | |
| *A61L 2/26* | (2006.01) | |
| *A61L 2/025* | (2006.01) | |
| *B08B 3/04* | (2006.01) | |

(52) U.S. Cl.
CPC .............. *A61C 19/002* (2013.01); *A61L 2/26* (2013.01); *A61Q 11/02* (2013.01); *B08B 3/12* (2013.01); *A61L 2/025* (2013.01); *A61L 2202/121* (2013.01); *A61L 2202/122* (2013.01); *A61L 2202/17* (2013.01); *B08B 3/047* (2013.01)

(58) Field of Classification Search
CPC ... A61C 19/002; A61L 2/26; A61L 2202/122; A61L 2202/121; A61L 2/025; A61L 2202/17; B08B 3/12; B08B 3/047; A61Q 11/02
See application file for complete search history.

(56) References Cited

U.S. PATENT DOCUMENTS

| | | | | |
|---|---|---|---|---|
| 3,871,395 A | * | 3/1975 | Murry .................. | A45C 11/005 134/107 |
| 3,973,760 A | * | 8/1976 | Browning ............... | A61L 2/025 366/111 |
| 6,203,756 B1 | * | 3/2001 | Lin ......................... | A61L 2/186 422/28 |
| 2013/0192647 A1 | * | 8/2013 | Ledel ..................... | A61B 1/123 134/22.1 |

FOREIGN PATENT DOCUMENTS

JP          2008049233     *  3/2008   ............... B08B 3/12

* cited by examiner

*Primary Examiner* — Sean E Conley
*Assistant Examiner* — Brendan A Hensel
(74) *Attorney, Agent, or Firm* — Boyle Fredrickson, S.C.

(57) ABSTRACT

A system for ultrasonic cleaning of dental appliances provides nested containers adapted to communicate ultrasonic energy therethrough to provide cleaning of a dental appliance contained within the innermost container using a standard ultrasound machine without cross-contamination with liquid from the main ultrasound bath.

14 Claims, 3 Drawing Sheets

DENTAL APPLIANCE CLEANING SYSTEM WITH REDUCED CROSS CONTAMINATION

CROSS REFERENCE TO RELATED APPLICATIONS

This application claims the benefit of U.S. provisional application 62/615,759 filed Jan. 10, 2018 and hereby incorporated by reference.

BACKGROUND OF THE INVENTION

The present invention relates to cleaning systems for dental appliances, such as dentures, and in particular to an improved apparatus and method of cleaning dental appliances using ultrasonic cleaning systems.

Ultrasonic cleaning systems provide a tank coupled to one or more ultrasonic transducers that may conduct ultrasonic acoustic energy (for example, 20-400 kilohertz) through the tank wall (typically the bottom wall) into the tank cavity, the latter containing a cleaning solution. The acoustic energy induces cavitation in the cleaning solution drawing contaminants into the cleaning solution and ensuring that the cleaning solution penetrates cracks and seams in the object being cleaned. The agitation provided by the ultrasound may atomize the cleaning solution producing a fine mist above the cleaning solution, which is normally contained within the tank by a cover.

Dental offices may have one or more ultrasonic cleaning systems that are used, for example, as a preliminary step in removing debris and contamination from dental tools prior to sterilization using high-temperature steam or the like.

The same ultrasonic cleaning tanks may be used for cleaning dental appliances such as partials or dentures. In order to protect these appliances from contamination from the general tank's used cleaning solution, the appliance may be placed in a disposable "zipper" storage bag or a glass beaker partially filled with liquid. The ultrasonic energy is conducted from the cleaning solution of the ultrasound tank through the compliant storage bag or beaker and into the liquid contained therein to provide cleaning of the appliance without direct contact to the cleaning solution.

SUMMARY OF THE INVENTION

The present inventor has recognized that current practices for cleaning dental appliances creates a risk of comingled ultrasonic cleaning solutions and cross contamination between the used contaminated cleaning solution and the dental appliance both through tears or pinholes in the storage bag, and aerosolization or condensation drippage from the cover and/or by contamination of the dental appliance as it is removed from the storage bag whose outer surfaces and contacting surfaces of the zipper are in close contact with contaminated cleaning solution. Replacing the cleaning solution and cleaning the ultrasound tank before cleaning dental appliances is generally impractical.

The present invention provides a container system that may be used with conventional ultrasound cleaning systems to safely segregate dental appliances from contaminated ultrasound cleaning solution during episodic cleaning of dental appliances. In this regard, the invention provides a nested containers system including an outer supporting container providing acoustic coupling with the cleaning solution in the standard ultrasound cleaning tank and a lid to resist contamination by ultrasound-induced mist. An inner supported container fits within the outer container to maintain ultrasonic coupling therewith and to conduct acoustic energy into a volume holding isolated cleaning solution and the dental appliance. The inner supported container may include a lid in closing the space for the dental appliance and isolating the cleaning solution.

In this respect, the invention provides both improved separation between the contaminated fluid of the ultrasound tank and the dental appliance and reduced chance of contamination during removal of the dental appliance from the container system by a shielding the outer surfaces of the inner container from direct contact with contaminated cleaning solution and mist.

Other features and advantages of the invention will become apparent to those skilled in the art upon review of the following detailed description, claims and drawings in which like numerals are used to designate like features.

Figure 2:
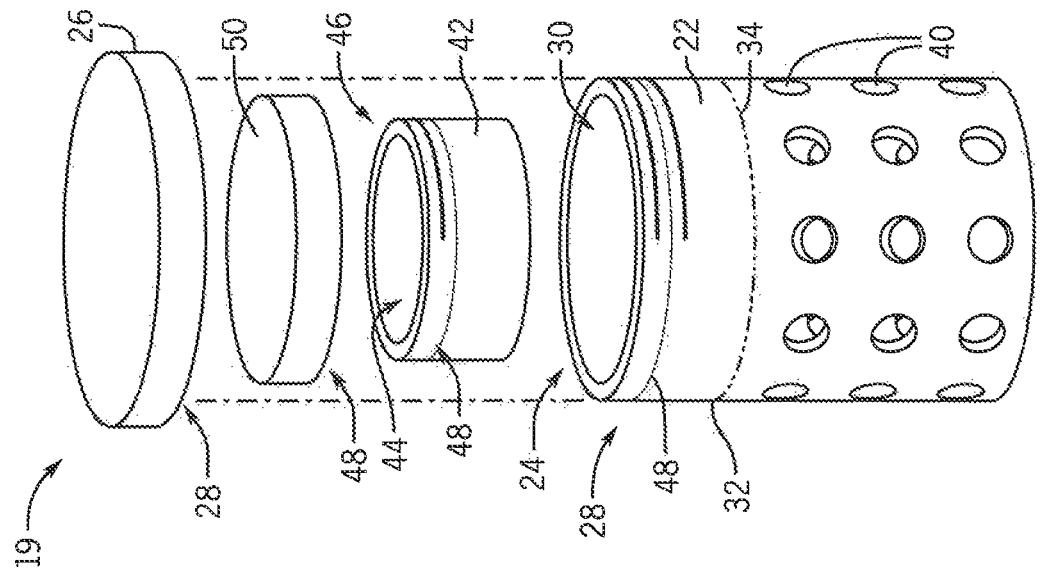
FIG. 2 is an exploded perspective view of the dual container system of the present invention showing the outer container and lid which together enclose the inner container and lid.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE PREFERRED EMBODIMENTS

Figure 1:
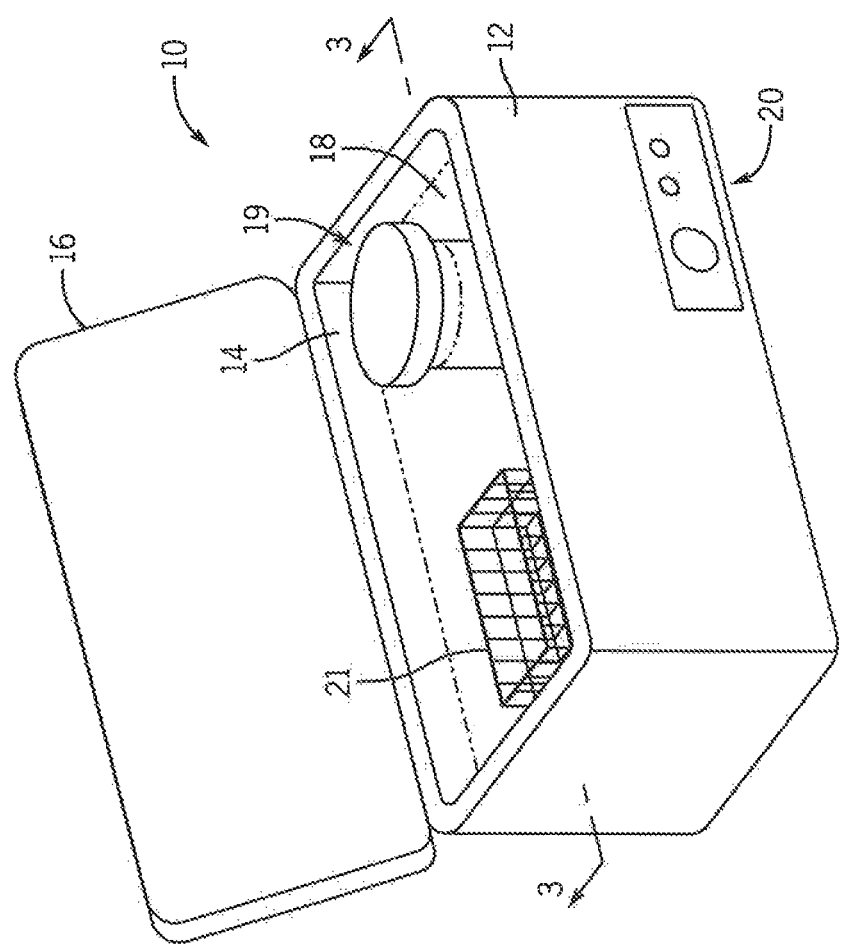
FIG. 1 is a simplified perspective view of a standard ultrasound cleaning machine showing a cage positioned within the tank for standard cleaning of dental tools and showing the outer container of the present invention positioned to one side of the cage.

Referring now to FIG. 1, an ultrasonic cleaning system 10 may provide for a housing 12 supporting a rectangular metal tank 14 typically constructed of stainless steel opening upward from the housing 12. The housing 12 may have a cover 16, for example, hinging along the back edge of an upper lip of the housing 12 or completely removable, to be closed over the upper open portion of the tank 14 to provide an enclosed volume within the tank 14. Ultrasound controls 20 may be positioned, for example, on a front surface of the housing 12 allowing for control of the ultrasonic cleaning process.

A cleaning solution 18, such as water, including a surfactant and disinfectant material may partially fill the tank 14 to cover an instrument cage 21, the latter being, for example, a wire basket freely admitting cleaning solution 18 therethrough which may hold dental instruments for easy removal while ensuring good contact with the cleaning solution. To a side of the instrument cage 21, and sized to easily share the tank, 14 is a container system 19 of the present invention for the cleaning of objects such as removable dental appliances as will be discussed. For normal operation, the cleaning solution 18 will be filled to a predefined level designated typically by the manufacturer and providing a fill height.

Referring now also to FIG. 2, the container system 19 may provide for an outer cylindrical container 22 open at an upper lip 24 that may receive a corresponding lid 26, for example, attached to the outer cylindrical container 22 by screw threads 28 therebetween or other similar attachment mechanism to provide a substantially enclosed and sealed inner volume 30 within the outer cylindrical container 22. The outer cylindrical container 22 and lid 26 may be constructed of a corrosion-resistant material such as stainless steel or the like sufficiently weighted so as to remain submerged in the cleaning solution 18 under its own weight to a level 32 beneath the upper lip 24 and without contact with the lid 26 without risk of tipping. In this respect the height of the outer cylindrical container 22 may be less than twice its width. Preferably the outer cylindrical container 22 has a weight of greater than four ounces and ideally greater than eight ounces for good coupling and stability. As an example, the height of the outer cylindrical container 22 may be approximately 5 inches and may have an inner diameter of 3.75 inches. A fill fiducial line 34 may be placed on the outer surface of the outer cylindrical container 22 to indicate a maximum liquid height when the outer cylindrical container 22 is placed within the metal tank 14 and its contained cleaning solution 18.

Figure 3:
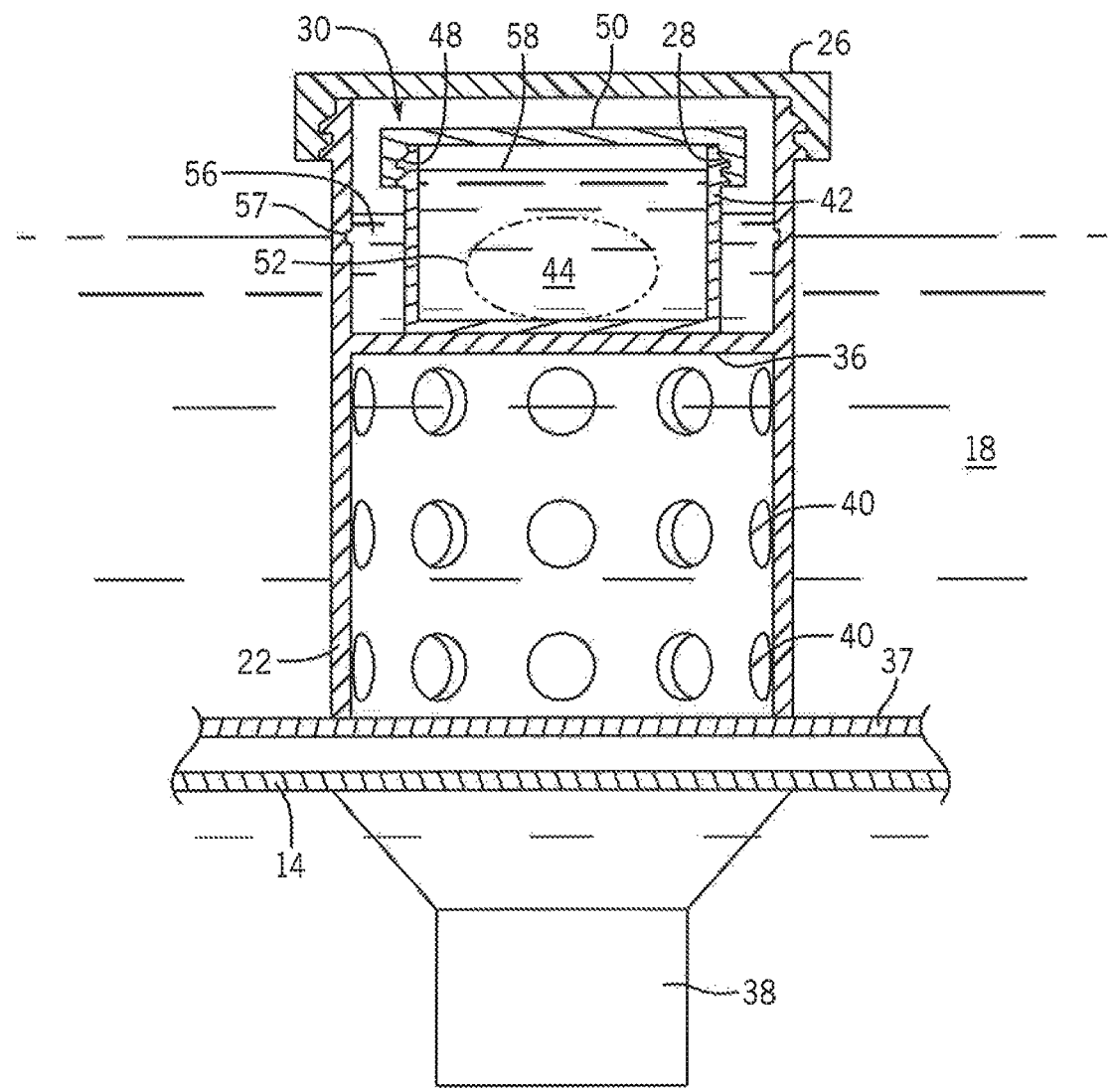
FIG. 3 is a fragmentary cross-sectional view along line 3-3 of FIG. 1 showing a false bottom of the outer container and fluid passage openings to ensure good fluid coupling through the false bottom.
Figure 4:
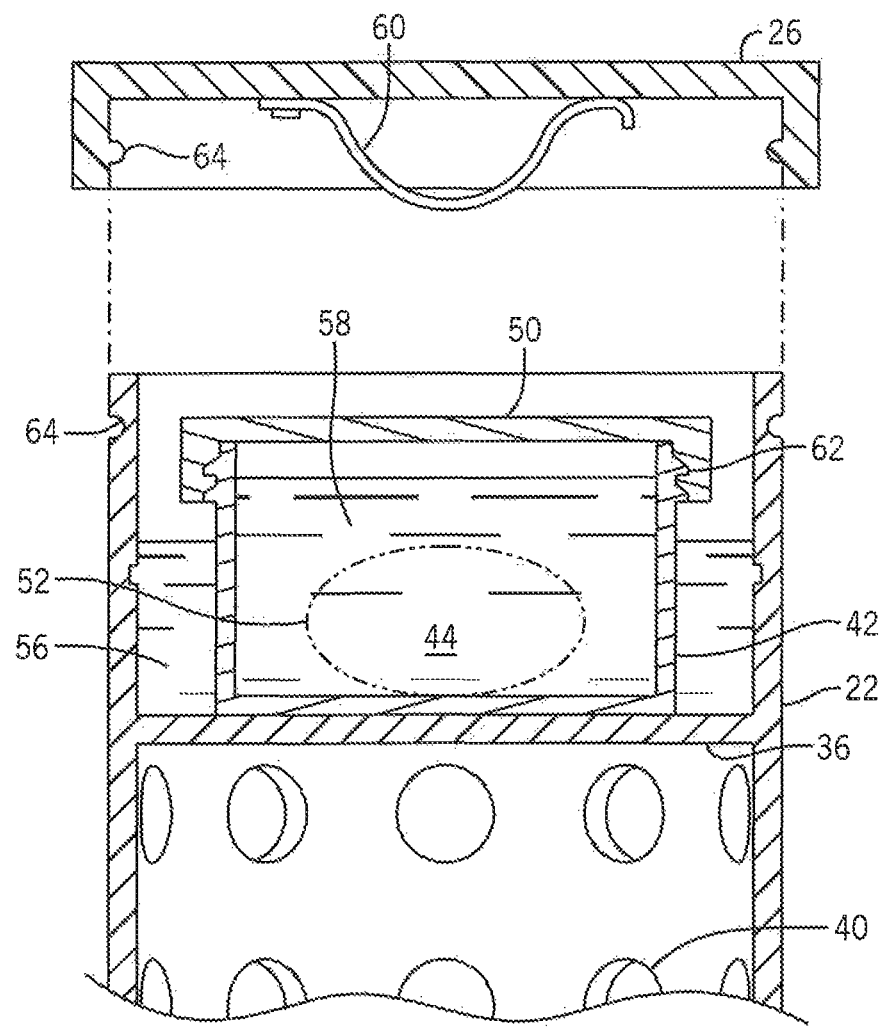
FIG. 4 is a fragmentary cross-sectional view similar to that of FIG. 3 showing an alternative design employing a lightweight inner container that may be disposed of after use for improved resistance to cross-contamination.

Referring also to FIG. 3, the outer cylindrical container 22 may rest on a spacer tray 37 or the like separated from the bottom of the tank 14 to prevent interference by the weight of the outer cylindrical container 22 with vibration of the lower wall of the tank 14 by one or more ultrasonic transducers 38 attached thereto and in order to work with conventional ultrasonic cleaning systems 10 having such a spacer tray 37.

The outer cylindrical container 22 may include a false bottom 36 extending horizontally above half the height of the outer cylindrical container 22 but below fill fiducial line 34 to partition and separate the volume 30 from a lower portion of the outer cylindrical container 22. In one example, the false bottom maybe two inches below the upper lip 24 of the outer cylindrical container 22. The outer walls in this lower portion of the outer cylindrical container 22 below the false bottom 36 may be perforated with multiple openings 40 to allow free conduction of cleaning solution 18 and ultrasonic energy into the space beneath the false bottom 36 and in contact with the false bottom 36. In this regard the false bottom 36 may be constructed to be substantially transparent to ultrasonic energy, for example, metal or the like. Ideally the openings 40 are such as to prevent an air bubble from being trapped against the underside of the false bottom 36.

An inner cylindrical container 42 fitting within the volume 30 may likewise provide an upwardly opening volume 44 closed at its bottom and terminating at upper lip 46. This upper lip 46 may also include threads including helical threads as well as "L" slots (for example as in a so called bayonet connection) or another secure closure 48 engaging the corresponding threads 48 of an inner lid 50 which may be attached to the inner cylindrical container 42 to seal the enclosed volume 44. A dental appliance 52 may be placed within this volume 44 and sealed therein by the lid 50. The inner cylindrical container 42 and lid 50 may have a weight sufficient to overcome any buoyancy and to provide good acoustic coupling with the false bottom 36. In one example, the inner container may have a height of approximately 1.7 inches and the diameter of approximately 3 inches.

During use, the inner cylindrical container 42 rests against the false bottom 36 and may receive ultrasonic energy therethrough also coupled by isolated cleaning solution 56 partially filling the space remaining around the inner cylindrical container 42 within the volume 30. A second isolated cleaning solution 58 partially fills the inner volume 44 of the inner cylindrical container 42 around the dental appliance 52. In one embodiment, an inner wall of the outer cylindrical container 22 defining the volume 30 may provide for a fill line 57 having a height such that when the isolated cleaning solution 56 is filled to the fill line 57 and then subsequently the inner cylindrical container 42 placed with its bottom against the upper surface of the false bottom 36, the height of the isolated cleaning solution 56 is well below the lid 50 attached to the inner cylindrical container 42.

It will be appreciated that a dental appliance 52 thus placed, is directly shielded from the cleaning solution 18 by sturdy metallic walls of the outer cylindrical container 22 resistant to tears or punctures and protected from contaminating mist by the lid 26. The dental appliance 52 is further separated from the cleaning solution 18, the walls of the inner cylindrical container 42, and the lid 50 within an isolated cleaning solution 58.

After cleaning, the inner cylindrical container 42 and lid 50 may be removed with the outer surfaces of these elements free from contamination that might be transferred to the dental appliance 52 upon removal of the dental appliance 52 from the inner cylindrical container 42. The lid 50 may then be removed to allow the dental appliance 52 to be extracted as cleaned by ultrasonic energy without contamination.

Referring now to FIG. 5, any need to clean the inner cylindrical container 42 to prevent cross-contamination between successive dental appliances 52 may be eliminated through the use of a disposable or low-cost multiuse inner cylindrical container 42 and lid 50, for example, constructed of a lightweight sterilizable polymer such as polyethylene or the like. In this embodiment, lower inner surface of the lid 26 may provide for a spring clip 60 or the like or a standoff sized to press downward on the lid 50 of the inner cylindrical container 42 to prevent buoyancy (possible as a result of the lightweight material of the inner cylindrical container 42) from preventing good acoustic coupling between the false bottom 36 of the outer cylindrical container 22 and the bottom of the inner cylindrical container 42. In this regard, the lid 50 may be attached to the inner cylindrical container 42 by a snap connection 62 instead of threads, the former that may be firmly engaged by the spring clip 60 during attachment of the lid 26 eliminating possible oversight in sealing the inner cylindrical container 42 by a user. A similar snap fittings 64 may be used to attach the lid 26 to the outer cylindrical container 22 eliminating the need for time-consuming rotation of the lid to engage the two and ensuring positive sealing action. In this regard the inner cylindrical container 42 may be carefully dimensioned to ensure proper engagement with the spring clip 60 and the availability of this auto closure feature. The lids 26 and 50 may include an elastomeric seal such as O-rings to improve their sealing capability.

Various features of the invention are set forth in the following claims. It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

What is claimed is:

1. A system for cleaning dental appliances in an ultrasonic cleaner of a type having a tank providing ultrasonically energized liquid held at a liquid height above the tank bottom, the system comprising:
    a shield container providing walls including a bottom wall and peripheral upstanding walls terminating at an upper lip;
    a removable shield lid attachable to the upper lip of the shield container to define an isolated shield volume between the removable shield lid and the shield container bottom wall sized to receive a dental appliance;
    a shield stand having a lower portion adapted to rest against an upper surface of the tank bottom of the ultrasonic cleaner to support the shield container bottom wall above the tank bottom and the upper lip of the shield container and removable shield lid above the liquid height;
    wherein the shield stand and shield container have a weight sufficient to hold the shield stand stably against the tank bottom against forces of buoyancy; and
    wherein at least one shield container wall in contact with the liquid is adapted to conduct ultrasonic energy from the ultrasonic cleaner tank into the defined isolated shield volume for cleaning of material placed in the defined isolated shield volume without permitting a flow of liquid from the ultrasonic cleaner tank into the defined isolated shield volume;
    further including a secondary container sized to be held within the isolated shield volume to sealably retain isolated cleaning liquid and the dental appliance.

2. The system for cleaning dental appliances of claim 1 wherein the removable shield lid sealably attaches to the shield container to prevent liquid flow therepast.

3. The system for cleaning dental appliances of claim 2 wherein the removable shield lid sealably attaches to the shield container by interengaging threads.

4. The system for cleaning dental appliances of claim 1 wherein the shield stand includes openings allowing liquid to flow underneath the shield container in contact with the shield container bottom wall when the shield stand is supported against the tank bottom.

5. The system for cleaning dental appliances of claim 1 wherein the secondary container provides a secondary bottom wall adapted to rest against the bottom wall of the shield container and upstanding peripheral walls terminating at an upper rim releasably attached to a secondary lid to enclose the defined the secondary isolated volume.

6. The system for cleaning dental appliances of claim 5 wherein the shield container has an inner fill line defining a desired volume of transfer liquid received in the shield container and wherein the upstanding peripheral walls of the secondary container terminate above the height of the desired volume of transfer liquid after displacement by a volume of the secondary container.

7. The system for cleaning dental appliances of claim 6 wherein the secondary container has a weight to rest without floating on the bottom wall of the shield container in a presence of transfer liquid of the volume.

8. The system for cleaning dental appliances of claim 5 wherein the secondary lid provides a liquid-tight attachment to the secondary container.

9. The system for cleaning dental appliances of claim 6 wherein the secondary lid attaches to the secondary container by interengaging threads.

10. The system for cleaning dental appliances of claim 5 wherein the secondary container is held down by a retention element attached to at least one of the shield container and shield container lid.

11. The system for cleaning dental appliances of claim 10 wherein the retention element is a spring finger extending downward from the shield container lid to press against a top of the secondary lid of the secondary container.

12. The system for cleaning dental appliances of claim 1 wherein the secondary container is constructed of a polymer material.

13. The system for cleaning dental appliances of claim 1 wherein the shield container, the removable shield lid, and the shield stand are constructed of stainless steel.

14. The system for cleaning dental appliances of claim 1 wherein the shield container and the shield stand are fixedly attached to each other.

* * * * *